United States Patent [19]

Fisher

[11] Patent Number: 5,360,438
[45] Date of Patent: Nov. 1, 1994

[54] METHOD AND DEVICE FOR IMPROVING CRANIAL NERVE FUNCTION TO IMPROVE MUSCLE FUNCTION AND THEREBY OVERCOME VISUAL/PERCEPTUAL DYSFUNCTION

[76] Inventor: Mary R. Fisher, 508 Walnut St., Green Lane, Pa. 18054

[21] Appl. No.: 9,495

[22] Filed: Jan. 26, 1993

[51] Int. Cl.⁵ .............................................. A61N 1/36
[52] U.S. Cl. ......................................... 607/53; 607/141
[58] Field of Search ................... 607/53, 75, 115, 1 H

[56] References Cited

U.S. PATENT DOCUMENTS

| | | |
|---|---|---|
| 381,260 | 4/1888 | Leighton . |
| 411,689 | 9/1889 | Smith et al. . |
| 490,678 | 1/1893 | Price . |
| 575,658 | 1/1897 | Mayer . |
| 3,376,870 | 4/1968 | Yamamoto et al. ............... 607/141 |
| 3,527,230 | 9/1970 | Imamura . |
| 4,271,841 | 6/1981 | Friedman . |
| 4,331,163 | 5/1982 | Nomura . |
| 4,369,791 | 1/1983 | Friedman . |
| 4,603,697 | 5/1986 | Kamerling . |

*Primary Examiner*—William E. Kamm
*Assistant Examiner*—Scott M. Getzow
*Attorney, Agent, or Firm*—Panitch Schwarze Jacobs & Nadel

[57] ABSTRACT

A method and device for improving cranial nerve function to improve muscle function and thereby overcome visual/perceptual dysfunction of a user includes a voltage source and electrodes positioned on the user proximate a cranial nerve for receiving a voltage signal from the voltage source and for transmitting an electrical stimulus to the cranial nerve of the user. A timer is electrically connected to the voltage source and the electrodes for establishing a first predetermined period of time in which the voltage signal is provided to the electrodes and a second predetermined period of time in which the voltage signal is suppressed.

9 Claims, 2 Drawing Sheets

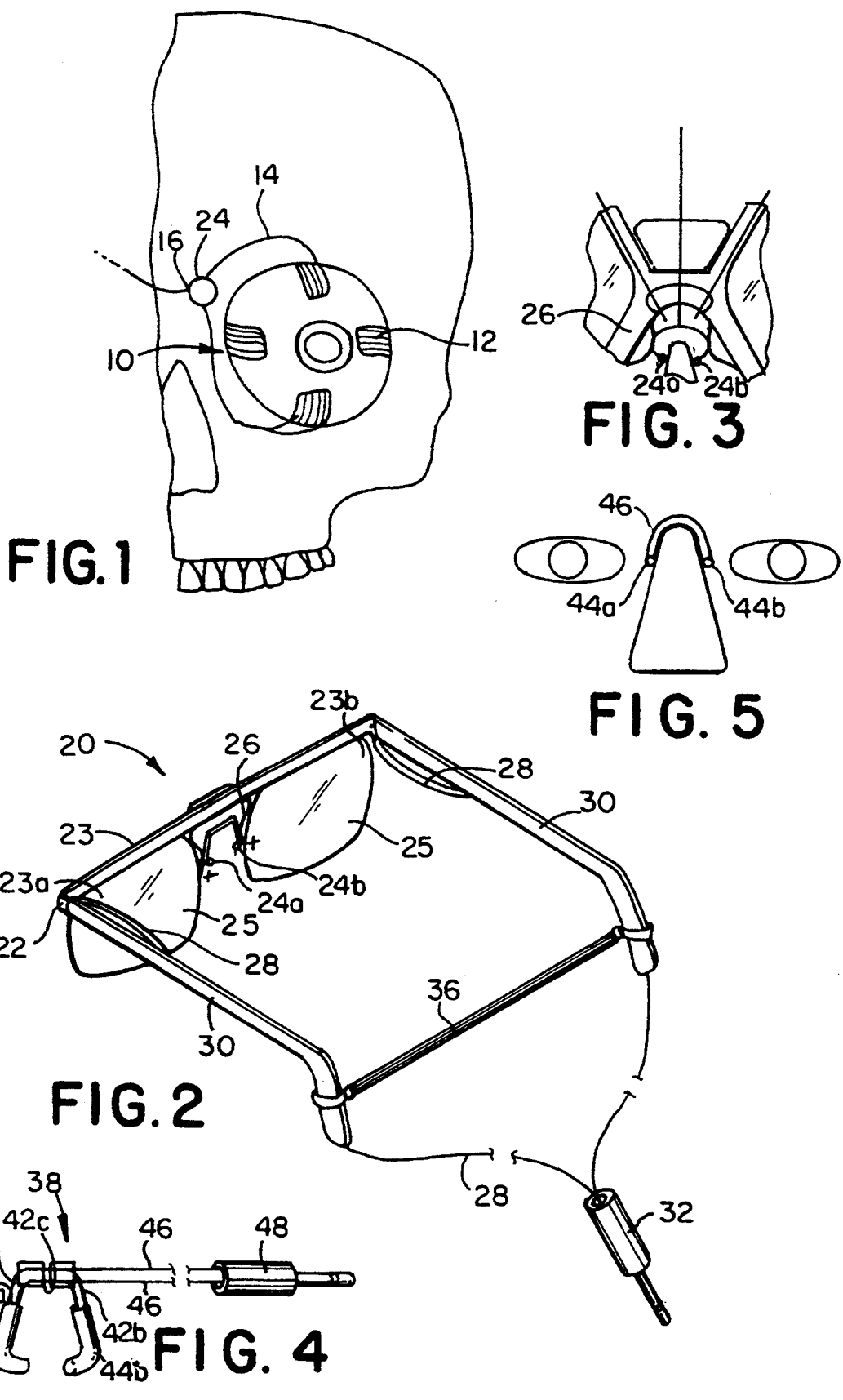

METHOD AND DEVICE FOR IMPROVING CRANIAL NERVE FUNCTION TO IMPROVE MUSCLE FUNCTION AND THEREBY OVERCOME VISUAL/PERCEPTUAL DYSFUNCTION

FIELD OF THE INVENTION

The present invention relates to an occulomotor nerve enhancement device and, more particularly, to a method and device for improving cranial nerve function so as to improve muscle performance and thereby overcome visual/perceptual dysfunction of a user.

BACKGROUND OF THE INVENTION

Many people suffer from visual dysfunction which is often a result of inadequate innervation to the muscles associated with the eyes. Each eye is supported by six extra occular skeletal muscles which coordinate the movements of the eye allowing the eyes to move synchronously. The extra occular muscles of each eye function in combination resulting in normal or standard visual perception. When the extra occular muscles do not function properly, perceptual errors occur as a result of the misalignment of the eyes. This dysfunction relative to denervation is characterized by in the loss of controlled eye movement which may cause the eye to "drift". A person suffering from the resulting muscle dysfunction is only capable of properly focusing with one eye at a time, thereby reducing image and depth perception.

It is believed that this type of eye muscle dysfunction is due in part to minute lapses in stimulation of the muscles from certain nerve sources, particularly the third, fourth and possibly sixth cranial nerves. The muscle dysfunction results in the transmission of wrong information to the brain, thereby fostering functional problems in many areas such as academics, leisure, and work. Typical behavior of an individual suffering from such visual dysfunction includes clumsiness, frequent spills, poor hand-eye coordination during target sports, etc. Inadequate muscle stimulation is also believed to cause, at least in part, dyslexia, attention deficit disorder, perceptual aberrations, strabismus and ptosis.

Many times people with visual dysfunction turn to surgery to attempt to correct the muscle condition. However, as with most surgical procedures, there are many risks involved which increase the risk of the reduction of or even loss of sight. Additionally, surgical procedures primarily offer cosmetic results. Because these surgical techniques have not been adequately perfected, many people are not in favor of and avoid this solution.

Additionally, there are noninvasive therapeutic techniques available for strengthening the eye muscles. These techniques include eye muscle exercises and the placement of a patch over the user's eye having normal muscle function which strengthens the weak muscles in the other eye through passive exercise. These techniques typically do not produce significant improvements. Furthermore, it is difficult to persuade young children to wear the patch because of teasing by other children.

The present invention is directed to a noninvasive method and device for improving innervation to extra occular muscles to improve the muscle function of a user's eye and thereby overcome visual/perceptual dysfunction. The device, in one embodiment, is placed proximate to the inner canthus or bridge of the nose and a low voltage electrical stimulus is intermittently applied to the user. By providing a cyclic flow of electrons to the nerve bifurcation located at the inner canthus, nerve function is enhanced, producing enriched action potential which improves synapses and as a result improves muscle function. The stimulated muscles prevent the drifting of the eye, thereby improving visual perception by assisting in focusing both eyes on a single location.

SUMMARY OF THE INVENTION

Briefly stated, the present invention is directed to a device for improving cranial nerve function to improve muscle function and thereby overcome visual/perceptual dysfunction of a user. The device comprises a voltage source and electrode means which are positionable on the user proximate a cranial nerve for receiving a voltage signal from the voltage source and for transmitting an electrical stimulus to the cranial nerve of the user. Timing means are electrically connected to the voltage source and the electrode means for establishing a first predetermined period of time in which the voltage signal is applied to the electrode means and a second predetermined period of time in which the voltage signal is suppressed.

The present invention is also directed to a method for improving cranial nerve function to improve muscle function and thereby overcome visual/perceptual dysfunction of a user. The method comprises the steps of assessing a base line reading rate for the user, determining the degree of visual dysfunction suffered by the user as a result of the base line reading rate, and establishing an electrical stimulation treatment plan for the user. Electrodes are placed on the user proximate a cranial nerve and the electrodes are connected to a voltage source. A voltage signal is applied to the electrodes in accordance with the established treatment plan thereby causing the electrodes to transmit an electrical stimulus to the cranial nerve. The application of the electrical signal is timed in accordance with the established treatment plan such that the electrical stimulus is applied to the cranial nerve for a first period of time and is suppressed for a second period of time.

BRIEF DESCRIPTION OF THE DRAWINGS

The foregoing summary, as well as the following detailed description of preferred embodiments will be better understood when read in conjunction with the appended drawings. For the purpose of illustrating the invention, there is shown in the drawings embodiments which are presently preferred, it being understood, however, that the invention is not limited to the specific methods and instrumentalities disclosed. In the drawings:

FIG. 1 is a anatomical diagram of an eye of a user to which has been applied an electrode of a device in accordance with the present invention;

FIG. 2 is a perspective view of a first embodiment of the electrode positioning portion of a device in accordance with the present invention;

FIG. 3 is an enlarged partial elevational view of an electrode structure used in the device of FIG. 2;

FIG. 4 is a perspective view of a second embodiment of the electrode positioning portion of a device in accordance with the present invention;

FIG. 5 is a schematic view of the electrode structure of the device of FIG. 4 positioned on the nose of a user;

DESCRIPTION OF THE PREFERRED EMBODIMENTS

Figure 6:
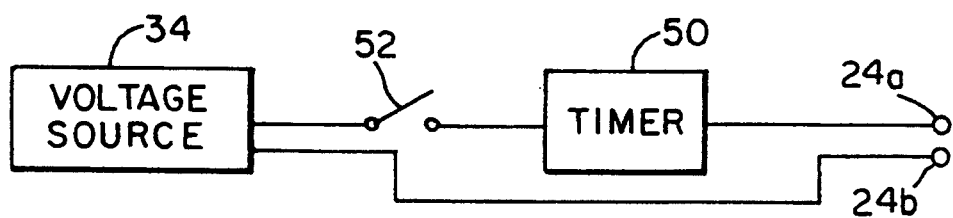
FIG. 6 is a functional schematic block diagram of a circuit used in conjunction with the device of FIGS. 2 and 4.

Referring to the drawings, wherein like numerals indicate like elements throughout, there is shown in FIG. 1 an anatomical diagram of an eye 10 of a user. A plurality of extrinsic skeletal muscles 12 surround and are attached to the outer portion of the eye 10 and are responsible for controlling the eye's movements. Each extra occular muscle 12 is innervated by third and fourth cranial nerves (not shown) which control the contraction and relaxation of the eye muscles 12. To effect smooth eye movement and proper visualization, the contraction of one eye muscle must be accompanied by the relaxation of an antagonistic muscle. More particularly, a nerve commonly known as the third cranial nerve 14 is connected to and transmits an electrical stimulus to the specific extra occular muscles 12 to provide control of the eye muscles, particularly with respect to controlling the direction of eye movement. Each eye 10 is provided with an appropriate electrical stimulus which causes the eves to move synchronously with respect to one another. If each eye is not provided with a complementary stimulus, the eye muscles do not move synchronously which many times results in one of the eyes "drifting" or moving to the outer corner. Such a condition is often referred to as a lazy eye condition or strabismus.

It is believed that by applying an external electrical stimulus to the third cranial nerve 14 or one or more of the other cranial nerves (not shown), particularly at the point where the third cranial nerve bifurcates 16, cranial nerve function will be improved resulting in improved eye muscle function and therefore coordination. The third cranial nerve bifurcation 16 is conveniently located at the inner canthus or bridge of the nose of the user. By applying an electrical stimulus to the third cranial nerve bifurcation 16, there is an increase in the action potential which in turn improves muscle function. Application of an electrical stimulus to other cranial nerves (not shown) also improves muscle function. By strengthening the eye muscles 12, greater eye movement control can be achieved which can result in improved vision.

Referring to FIG. 2, there is shown a first preferred embodiment of a device 20 for improving cranial nerve function to improve muscle function and thereby overcome visual dysfunction. In the present embodiment, the device 20 is incorporated into a pair of eye glasses 22 for providing an electrical stimulus to only the third cranial nerve. However, it is to be understood by those skilled in the art that the device 20 may be implemented in other suitable arrangements and may provide electrical stimulus to one or more other cranial nerves.

The eye glasses 22 include an eye glass front frame 23 having a first end 23a and a second end 23b. A pair of earpieces 30 are hingedly connected to each end 23a, 23b of the front frame 23. The earpieces 30 are attached in a manner such that they may be in a first extended position in which the they are perpendicular to the front frame 23 and a second folded, storage position in which they are parallel to and proximate the eye glass front frame 23 in a manner well known in the eye glass art. The eye glasses 22 may either be of a prescriptive nature if the user requires corrective lens or may be of a cosmetic nature and designed specifically for the purpose of implementing the device. It is to be understood by those skilled in the art that any type of eye glasses 22 could be used without departing from the scope and spirit of the present invention.

A pair of nose pads 26 are mounted on the portion of the front frame 23 which is adjacent the nose of the user. A separate electrode 24a, 24b is mounted to each nose pad 26. The electrodes 24a, 24b are preferably made of an electrically conductive material such as, but not limited to, silver, copper or aluminum. It is to be understood by those skilled in the art that any electrically conductive material can be used as an electrode without departing from the scope and spirit of the present invention. One of the electrodes 24a is preferably designated a negative electrode and the other electrode 24b is preferably designated a positive electrode. The electrodes 24a, 24b are preferably attached to the nose pads 26 by an elastic, generally springy material (not shown) so that the electrodes 24a, 24b gently clamp onto the bridge of the nose of the user with sufficient pressure to provide good electrical contact in a manner which is not uncomfortable to the user.

Wires 28 are connected to each electrode 24a, 24b for providing a means for applying a voltage signal between or across the electrodes 24a, 24b. The wires 28 extend from each electrode 24a, 24b along the eye glass front frame 23 adjacent each lens 25 and further along each earpiece 30. The wires 28 are combined by a connector plug 32 of a type well known in the art which plugs into a predetermined voltage source 34 (FIG. 6) for providing a voltage signal to the electrodes 24a, 24b. The voltage source 34 is preferably a DC voltage source which is capable of varying its output voltage from 0.01 volt to 10 volts. Other DC voltage ranges will be apparent to those skilled in the art. An elastic band 36 may be attached to the end of the earpieces 30 to secure the glasses 22 to the user's head and to assist in maintaining good electrical contact between the electrodes 24a, 24b and the nose of the user.

Referring to FIG. 3, there is shown an enlarged elevational view of the electrodes 24a, 24b of the device 20 and, more particularly, illustrating the relationship between the electrodes 24a, 24b and the bridge of the nose of the user. In the preferred embodiment, the electrodes 24a, 24b are situated generally symmetrically with respect to the user's nose and are in generally continuous electrical contact with the bridge of the nose at approximately the point where the third cranial nerve 14 bifurcates and where the third cranial nerve is closest to the surface of the skin. The electrodes 24a, 24b are further situated such that when a voltage is applied in a manner hereinafter described, a small electrical current flows from one electrode through the third cranial nerve to the other electrode depending upon the polarity of the applied voltage. The current flow improves the action potential of the third cranial nerve 14 which thereby improves occular muscle function.

Referring to FIG. 4, there is shown a second preferred device 38 for improving third cranial nerve function in accordance with the present invention. A generally U-shaped support 40 includes a first arm 42a and a second arm 42b connected together by a bight portion 42c. A pair of electrodes 44a, 44b are connected to the support 40 such that a first electrode 44a is connected to the first arm 42a and the second electrode 44b is connected to the second arm 42b. The electrodes 44a, 44b are of a similar type as described above with respect to the first embodiment and as such will not be discussed further. The support 40 is preferably made out of an elastic material such as plastic or alternatively contains a spring so that the support 40 may be easily clamped to the bridge of the nose of the user with sufficient force to provide good electrical contact between the electrodes and the skin of the user and yet not be uncomfortable to the user. However, it is to be understood by those skilled in the art that the support 40 may be made out of any other suitable material without departing from the scope and spirit of the present invention. A wire 46 extends from each electrode 44a, 44b to the bight portion 42c of the support 40. The wires 46 are connected together by a connector plug 48 which is inserted into the voltage source 34 (FIG. 6) to provide a voltage signal to the electrodes 44a, 44b in a manner which will hereinafter be described.

Referring to FIG. 5, the support 40 is straddlingly positioned over the bridge of the nose of the user such that a first arm 42a of the support 40 is located on a first side of the nose and the second arm 42b of the support 40 is located on a second side of the nose. The electrodes 44a, 44b are thus positioned proximate to the third cranial nerve bifurcation 16 which, as stated above, is the location in which the third cranial nerve is closest to the surface of the skin. The support 40 is preferably clamped onto the bridge of the nose such that a slight pressure is applied by the electrodes 44a, 44b to the third nerve bifurcation 16. The electrodes 44a, 44b intermittently transmit an electrical stimulus to the third cranial nerve bifurcation 16 as will be described in detail hereinafter.

The above described embodiments relate to apparatus employed for stimulation of the third cranial nerve at a point proximate the bridge of the nose of the user where the third cranial nerve bifurcates and is closest to the surface of the skin of the user. It should be clearly understood by those skilled in the art that modifications could be made to the above described embodiments for the purpose of stimulating the third cranial nerve at any other suitable location. It should also be clearly understood that the present invention is not limited to a device for stimulation of the third cranial nerve. Any other cranial nerve such as the forth or sixth cranial nerve may be alternatively stimulated for achieving the same purpose. Moreover, it will be appreciated by those skilled in the art that two or more cranial nerves may be simultaneously stimulated or may be alternatingly stimulated. For example, by placing one or both of the electrodes at the point of the superior orbital fissure, the third cranial nerve (occular motor), fourth cranial nerve (trochlear) and sixth cranial nerve (abducens) come together and, hence, could all be simultaneously stimulated to improve the function of all extra occular muscles at the same time. The electrodes could be applied to the superior orbital fissure by attachment to each of the earpieces 30 of the glasses 22 of FIG. 2 at a point where the earpieces pass the superior aspect of the zygomatic bone of the face of the user (not shown). Electrodes at this location could also be employed in addition to the above-described electrodes 24a and 24b in order to supplement the above-described third cranial nerve stimulation electrodes. Thus, it should be clearly understood by those skilled in the art that the present invention relates to stimulation of at least one cranial nerve and is not limited to a particular cranial nerve, a particular number of cranial nerves or a particular location for stimulation of the cranial nerve(s).

Figure 7:
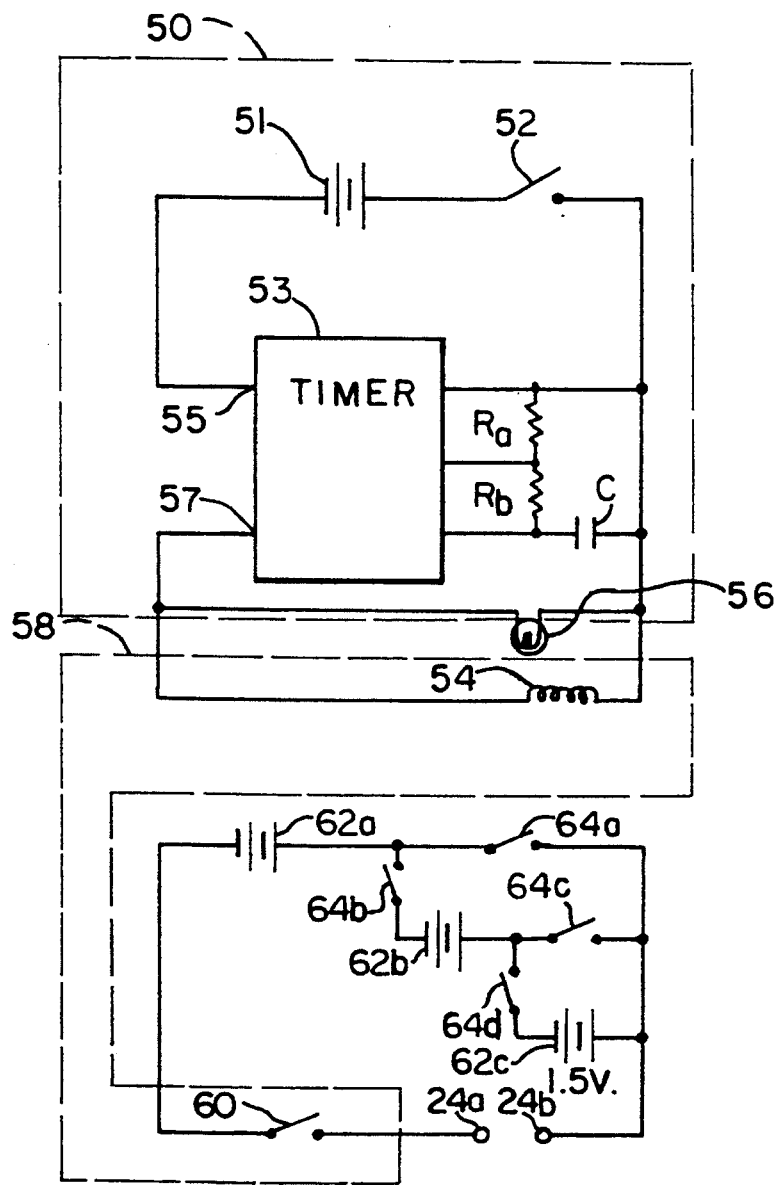
FIG. 7 is a more detailed schematic diagram of the circuit depicted in FIG. 6.

Referring to FIGS. 6 and 7, there is shown a general block diagram and a more detailed schematic diagram of the circuitry preferred for providing an electrical stimulus to a cranial nerve and, in the present embodiment, the third cranial nerve bifurcation 16. A voltage source 34 which in the present embodiment is preferably DC, provides a low DC voltage signal to the electrodes 24a, 24b for nerve stimulation. It is to be understood by those skilled in the art that the voltage source 34 may be any suitable DC, AC or other source without departing from the scope and spirit of the present invention. The voltage source 34 is preferably capable of supplying a voltage signal which is within a range from about 0.01 volt to 10.0 D.C. volts. The voltage level may be fixed or adjustable within the above-described range and the voltage source may be incorporated into any suitable type or size housing. For example, the voltage source may be a small, fixed voltage source which is attached to or supported by one of the earpieces 30 in a manner similar to a hearing aid or may be a larger adjustable voltage desk top unit. It is to be understood by those skilled in the art that the voltage may be adjusted to a fixed level to be applied during the course of treatment or the voltage level may vary during the entire course of treatment without departing from the scope and spirit of the present invention.

A timer 50 is preferably positioned between the voltage source 34 and the electrodes 24a, 24b. In the preferred embodiment, the timer 50 is preferably electrically isolated from the voltage source 34. A switch 52 is also connected between the timer 50 and voltage source 51 for activating the circuitry and causing a voltage signal from the voltage source 34 to be selectively applied to the electrodes 24a, 24b or for the voltage signal to be suppressed. The timer 50 is shown in greater detail in FIG. 7 and preferably includes an integrated circuit (IC) timer 53 which is connected to a pair of timing control resistors $R_a$, $R_b$. An external capacitor C cooperates with resistors $R_a$ and $R_b$ to determine the on time/off time duty cycle of the IC timer 53. The resistors $R_a$, $R_b$ and the capacitor C essentially form a voltage divider timer. The capacitor C charges through resistors $R_a$ and $R_b$ and discharges through resistor $R_b$ only. A separate voltage source 51, in the illustrated embodiment a battery, supplies a bias voltage to an input pin 55 located on the IC timer 53. In the preferred embodiment the IC timer 53 is a commercially available "555" timer chip. However, it is to be understood by those skilled in the art that any other timer circuit or chip may be used without departing from the scope and spirit of the present invention.

The IC timer 53 preferably functions so that a DC voltage signal is applied to the electrodes 24a, 24b for a first predetermined time period and the voltage signal is suppressed for a second predetermined time period. The length of the time periods is established by the values of $R_a$, $R_b$ and C. In the preferred embodiment, the first predetermined time period is approximately six seconds and the second predetermined time period is approximately 24 seconds providing a 1:4 on/off duty cycle which is repeated every thirty seconds i.e. the voltage signal is applied to the electrodes about one-fifth of the time during a treatment period. However, it is to be understood by those skilled in the art that the first predetermined time period may be adjustable and may vary in a range of from 1 to 15 seconds. The second predetermined time period may also be adjustable and vary in a range of 15 to 29 seconds. In order to change the first predetermined time period and second predetermined time period the timing of the IC timer 53 must be changed by changing the values of $R_a$, $R_b$ and C. To achieve the preferred time periods discussed above, C=100 microfarads and $R_a$ and $R_b$ each equal 100 Megaohms. If desired the resistor $R_a$, $R_b$ and the capacitor C may be individually adjustable for maintaining timing flexibility. Alternatively preselected values of each of these components may be established utilizing suitable rotary or detent switches (not shown) in a manner well known to those skilled in the art.

An indicator is associated with the IC timer 53 for indicating to a user when the IC timer 53 is in the on portion of the duty cycle and a voltage signal is applied to the electrodes 24a, 24b. The indicator is in a first state when the IC timer 53 is in the first predetermined time period (on) and is in a second state when the IC timer 53 is in the second predetermined time period (off). The indicator is preferably a visual indicator such as a light bulb 56 which is connected to the output pin 57 of the IC timer 53. In the preferred embodiment, when the IC timer 53 is in the first predetermined time period (i.e., on portion of the duty cycle), a voltage is applied across the light bulb 56 and the light bulb 56 is illuminated and when the IC timer 53 is in the second predetermined time period, no voltage is applied across the light bulb 56 and the light bulb 56 is not illuminated. However, it is to be understood by those skilled in the art that any other type of indicator could be used or no indicator could be used without departing from the scope and spirit of the present invention.

A relay mechanism 58 is also associated with the IC timer 53 for controlling when the voltage signal is applied to the device 20. The relay mechanism 58 comprises a relay coil 54 which controls the opening and closing of relay contacts 60 in a manner well known in the art, thereby controlling when a voltage signal is applied to the electrodes 24a, 24b. When current flowing through the relay coil 54 reaches a predetermined minimum value, the relay mechanism 58 is actuated and the normally open contacts 60 are closed. The relay coil 54 receives current from an output pin 57 associated with the IC timer 53. The frequency at which a voltage appears on the output pin 57 is determined by the duty cycle of the IC timer 53 as established by the values of $R_a$, $R_b$ and C. When the contacts 60 are closed, a voltage signal is applied to the electrodes 24a, 24b of the device 20. When the current through the coil 54 falls below a predetermined minimum value, i.e. when the IC timer 53 is in the off portion of the duty cycle, the relay contacts 60 are open and the voltage signal is suppressed from or removed from the electrodes 24a, 24b.

The voltage supply 34, in the embodiment shown in FIG. 7, is designed such that the user can select the voltage level of the voltage signal applied to the electrodes 24a, 24b from among three specific voltages. In the preferred embodiment, the voltage source 34 comprises three separate 1.5 volt sources or batteries 62 which are separated from one another by a series of switches 64a-64d. However, it is to be understood by those skilled in the art that any size voltage source or any number of voltage sources or batteries can be used without departing from the scope and spirit of the present invention. It should also be understood that the voltage source 34 may be infinitely or discretely adjustable within a broader voltage range, preferably extending from about 0.01 volt to 10.0 volts. It should also be understood that the voltage signal from the voltage source 34 may be fixed (i.e. not adjustable) at any desired voltage within the foregoing range.

In the preferred embodiment, the user can select to apply a 1.5 volt signal, a 3.0 volt signal or a 4.5 volt signal to the electrodes 24a, 24b depending upon the position of the switches 64a-64d. If the user wishes to apply a 1.5 volt signal, then the user closes a first switch 64a and places switches 64b, 64c and 64d in an open state (as shown) thereby connecting only 1.5 volt battery 62a to the electrodes 24a and 24b and preventing the other batteries 62b, 62c from applying a voltage signal. If the user wishes to apply a 3 volt signal, the first and fourth switches 64a and 64d are placed in an open state and the second and third switches 64b, 64c are in a closed state, thereby connecting 1.5 volt batteries 62a and 62b in series. If the user wishes to apply a 4.5 volt signal, switches 64b and 64d are in a closed state and switches 64a and 64c are in an open state, thereby connecting all three 1.5 volt batteries (62a, 62b and 62c) in series. As discussed above, regardless of which DC voltage is selected, the timer 50 through the relay mechanism 58 controls the time period during which the voltage signal is actually applied to the user through the electrodes 24a, 24b.

Before a user is treated with the above-described device 20, a baseline reading rate should be assessed for the user. Typically, the user is asked to read aloud a passage containing carefully selected material of a particular reading level and the user's reading speed and accuracy are measured. The baseline reading rate is normally determined in terms of words per minute read. Typically, the reading accuracy is measured as the number of errors per average number of words. These errors can include but are not limited to mistakes such as letter inversion, and deleting, inserting or reversing letters in one or more words in the passage. Once a baseline reading rate is determined, the degree of visual/perceptual dysfunction suffered by the user can be generally determined by a trained professional as a result of an analysis of the baseline reading rate and personal observation. For example, the reading rate can indicate the presence of a condition such as dyslexia or the effects of strabismus, ptosis and attention deficit disorder. A treatment plan is established for the user based upon the determined degree of visual/perceptual dysfunction of the user.

When the device 20 is to be used for treatment in accordance with the established treatment plan, the electrodes 24a, 24b of the device 20 are placed on the bridge of the nose of the user or in some other suitable location for cranial nerve stimulation. A voltage source 34 is connected to the electrodes 24a, 24b in the manner described above. A voltage signal at a selected voltage level is intermittently applied to the electrodes 24a, 24b in accordance with an on/off duty cycle in accordance with the treatment plan thereby causing the electrodes 24a, 24b to apply an electrical stimulus to the third cranial nerve bifurcation 16 or such other cranial nerve or may be desired to be stimulated in accordance with the established treatment plan. The application of the electrical stimulus to the third cranial nerve is timed such that the electrical stimulus is transmitted for a first period of time and is suppressed for a second period of time, preferably at a 4:1 duty cycle as described above. Typically, during treatment different voltage levels are applied to the user under controlled conditions to empirically determine which voltage level provides the most improvement to the user's reading rate.

After the user has been treated by the device for a prescribed period of time, the reading rate for the user is again measured to determine what improvement, if any, the user has obtained by way of increased speed and accuracy. The treatment plan may be modified depending upon the results achieved.

Below is a table representing a study performed on five subjects having differing degrees of visual/perceptual dysfunction which were treated by the device 20 of the present invention at a 4:1 on/off duty cycle using different voltage levels and the resulting reading rates.

TABLE I

|  | Base reading rates | Average volts | Reading rates at 1½ | Average | Reading rates at 3 Volts | Average Volts | Reading rates at 4½ | Average |
|---|---|---|---|---|---|---|---|---|
| Subject 1 | 180,153 | 167 | 252,234 | 243 | 202,216 | 209 | 261 216,252 | 243 |
| Subject 2 | 182,252 | 217 | 276,348 360,390 | 343 | 312,360 390 | 344 | 342 | 342 |
| Subject 3 | 340 352,335 | 343 | 612,564 330,290 | 449 | 425,417 374,296 300 | 362 | 400 410 | 405 |
| Subject 4 | 152 |  | 192 |  | 168,216 | 192 |  |  |
| Subject 5 | 180 150 | 165 | 162 144 | 153 | 228 240 | 234 | 276 264 | 270 |

As can be seen from the table, different subjects had different improvements in reading rates over the base reading rate depending upon the particular voltage level applied. For some subjects, such as Subject 3, the most improvement in reading rate occurred at 1.5 volts. However for other subjects, such as Subject 5, the most improvement in reading rate occurred at 4.5 volts. In all cases, the device 20 helped to alleviate reading disorders and other associated conditions such as, dyslexia, attention deficit disorder, perpetual aberrations, cilliary muscle dysfunction, strabismus and ptosis. The result is that each user achieved a faster, more accurate reading rate and improved binocular function as a consequence of the improved muscle function to enhance innervation.

From the foregoing description, it can be seen that the present invention comprises a method and device for improving muscle function to overcome visual/perceptual dysfunction of a user. It will appreciated by those skilled in the art that changes could be made to the embodiments described above without departing from the broad inventive concept thereof. It is understood, therefore, that this invention is not limited to the particular embodiments disclosed, but is intended to cover all modifications which are within the scope and spirit of the invention as defined by the appended claims.

I claim:

1. A method for treating a user to improve muscle function to overcome visual/perceptual dysfunction of the user comprising the steps of:

assessing a base line reading rate for the user;
   determining the degree of visual/perceptual dysfunction suffered by the user as a result of the base line reading rate;
   establishing an electrical stimulation treatment plan for the user based upon the determined degree of visual/perceptual dysfunction;
   placing electrodes on the user proximate a cranial nerve;
   connecting a voltage source to the electrodes;
   applying a voltage signal to the electrodes in accordance with the established treatment plan thereby causing the electrodes to transmit an electrical stimulus to the cranial nerve; and
   timing the application of the voltage signal in accordance with the established treatment plan such that the electrical stimulus is transmitted to the cranial nerve for a first period of time and is suppressed for a second period of time.

2. The method according to claim 1, further comprising the step of reassessing the user's base line reading rate periodically during the treatment of the user and adjusting the treatment plan in accordance with the reassessment.

3. The method according to claim 1, further comprising the step of altering the level of the voltage signal applied depending upon changes in the reading rate of the user.

4. The method according to claim 1, further comprising the step of altering the timing of the voltage signal applied depending upon changes in the reading rate of the user.

5. A device for improving muscle function to overcome visual/perceptual dysfunction of a user comprising:

a voltage source;
   non-invasive, non-implantable electrode means for being temporarily positioned on the skin surface of the head of the user proximate a cranial nerve for receiving a voltage signal from the voltage source and transmitting an electrical stimulus to the cranial nerve of the user to improve cranial nerve function and muscle function and thereby provide enhanced eye movement control and overcome visual dysfunction; and
   timing means electrically connected to the voltage source and to the electrode means for establishing a first predetermined period of time within a range of from one second to fifteen seconds in which the voltage signal is provided to the electrode means and a second predetermined period of time within a range of from fifteen seconds to twenty-nine seconds in which the voltage signal is suppressed.

6. A device for improving muscle function to overcome visual/perceptual dysfunction of a user comprising:

a voltage source;
   non-invasive, non-implantable electrode means for being temporarily positioned on the skin surface of the head of the user proximate a cranial nerve for receiving a voltage signal from the voltage source and transmitting an electrical stimulus to the cranial nerve of the user to improve cranial nerve function and muscle function and thereby provide enhanced eye movement control and overcome visual dysfunction; and timing means electrically connected to the voltage source and to the electrode means for establishing a first predetermined period of time of approximately six seconds in which the voltage signal is provided to the electrode means and a second predetermined period of time of approximately twenty-four seconds in which the voltage signal is suppressed.

7. A device for improving muscle function to overcome visual/perceptual dysfunction of a user comprising:

a voltage source;

non-invasive, non-implantable electrode means for being temporarily positioned on the skin surface of the head of the user proximate a cranial nerve for receiving a voltage signal of approximately three volts D.C. from the voltage source and transmitting an electrical stimulus to the cranial nerve of the user to improve cranial nerve function and muscle function and thereby provide enhanced eye movement control and overcome visual dysfunction; and timing means electrically connected to the voltage source and to the electrode means for establishing a first predetermined period of time in which the voltage signal is provided to the electrode means and a second predetermined period of time in which the voltage signal is suppressed.

8. A device for improving muscle function to overcome visual/perceptual dysfunction of a user comprising:

a voltage source;

non-invasive, non-implantable electrode means for being temporarily positioned on the skin surface of the head of the user proximate a cranial nerve for receiving a voltage signal from the voltage source and transmitting an electrical stimulus to the cranial nerve of the user to improve cranial nerve function and muscle function and thereby provide enhanced eye movement control and overcome visual dysfunction;

timing means electrically connected to the voltage source and to the electrode means for establishing a first predetermined period of time in which the voltage signal is provided to the electrode means and a second predetermined period of time in which the voltage signal is suppressed; and support means comprising a clip for supporting the electrodes on the bridge of the nose of the user.

9. A device for improving muscle function to overcome visual/perceptual dysfunction of a user comprising:

a voltage source;

non-invasive, non-implantable electrode means for being temporarily positioned on the skin surface of the head of the user proximate a cranial nerve for receiving a voltage signal from the voltage source and transmitting an electrical stimulus to the cranial nerve of the user to improve cranial nerve function and muscle function and thereby provide enhanced eye movement control and overcome visual dysfunction;

timing means electrically connected to the voltage source and to the electrode means for establishing a first predetermined period of time in which the voltage signal is provided to the electrode means and a second predetermined period of time in which the voltage signal is suppressed; and support means comprising an elastic band for supporting the electrodes on the bridge of the nose of the user.

* * * * *